United States Patent [19]

Biswas

[11] Patent Number: 4,920,986
[45] Date of Patent: May 1, 1990

[54] URINARY INCONTINENCE DEVICE

[75] Inventor: Nicholas Biswas, Blacktown, Australia

[73] Assignee: Zedlani Pty. Limited, Parramatta, Australia

[21] Appl. No.: 108,276

[22] Filed: Oct. 13, 1987

[30] Foreign Application Priority Data

Oct. 14, 1986 [AU] Australia .............................. PH8486

[51] Int. Cl.⁵ .............................................. A61F 5/48
[52] U.S. Cl. .................................... 128/885; 128/834; 128/D25
[58] Field of Search .............. 128/1 R, D25, 128, 129, 128/98, 834, 885, 884

[56] References Cited

U.S. PATENT DOCUMENTS

| 2,638,098 | 5/1953 | Kulick | 128/D25 |
|---|---|---|---|
| 2,649,086 | 8/1953 | Sluijter | 128/1 R |
| 3,066,667 | 12/1962 | Berry | 128/1 R |
| 3,080,865 | 3/1963 | Vincent | 128/98.1 |
| 3,554,184 | 1/1971 | Habib . | |
| 3,646,929 | 3/1972 | Bonnar | 128/D25 |
| 3,661,155 | 5/1972 | Lindan | 128/128 |
| 3,705,575 | 12/1972 | Edwards | 128/D25 |
| 4,019,498 | 4/1977 | Hawtrey et al. | 128/D25 |
| 4,139,006 | 2/1979 | Corey . | |
| 4,290,420 | 9/1981 | Manetta | 128/D25 |

FOREIGN PATENT DOCUMENTS

| 2228464 | 12/1974 | France | 128/D25 |
|---|---|---|---|
| 2342717 | 9/1977 | France | 128/D25 |
| 1115727 | 5/1968 | United Kingdom . | |

Primary Examiner—C. Fred Rosenbaum
Assistant Examiner—Denise W. DeFranco
Attorney, Agent, or Firm—Ladas & Parry

[57] ABSTRACT

An intra-vaginal device to aid in controlling urinary incontinence, said device including a body with a forward portion to engage the anterior vaginal wall adjacent the bladder neck, which forward portion is expandable to close the bladder neck.

12 Claims, 6 Drawing Sheets

URINARY INCONTINENCE DEVICE

The present invention relates to devices for controlling urinary incontinence and to vaginal and rectal prolapse in females. Particularly, the invention relates to a device which may be removably inserted into the vagina.

Female urinary incontinence is a common problem and is particularly prevalent where damage to the bladder or neck of the bladder has occurred during child birth. In elderly female patients, urinary incontinence is wide spread.

In normal continent patients, in the erect posture, there is no descent of the bladder neck below the pelvic floor muscle, whereby equal distribution of intra-abdominal pressure to the bladder, bladder neck and pelvic urethra occurs, and continence is maintained. However, in stress incontinence, such equal pressure distribution is lost due to descent of the bladder neck below the pelvic floor muscle. On coughing or sneezing or physical exercise, i.e. when strain is put upon the bladder, an involuntary spurt of urine is released from the bladder. This involuntary urine release is unpleasant and embarrassing. The released urine may irritate the groin region and result in an offensive odour.

Vaginal and rectal prolapse are also quite common conditions in females, particularly those who have vaginally delivered one or more children. These conditions may be painful, and uncomfortable. Additionally, sexual intercourse may be impaired by occlusion of the vagina.

It is a generally accepted view that surgical treatment is most appropriate for cure of stress incontinence and vaginal and rectal prolapse. However, in elderly or infirm patients the risk of surgery is too great, so that often these conditions go untreated.

Previously proposed devices to treat incontinence and avoid recourse to surgery have generally been unsatisfactory. Particularly, they are cumbersome, difficult to use, need to be replaced frequently, are inadequate in cases of permanent incontinence and often fail to prevent involuntary urinary leakage.

One aspect of the present invention has as its object to provide an intra-vaginal device to aid in controlling vaginal and rectal prolapse.

There is disclosed herein an intra-vaginal device, comprising of two opposed limbs interconnected by a flexible base portion so as to be of a generally "U-shaped" configuration. One of the limbs is adapted to lie adjacent, i.e. engage an interior surface portion of the anterior vaginal wall and includes a cradle-like structure to lift the bladder base and bladder neck lying behind, i.e. located at an exterior surface portion of the anterior vaginal wall opposite the interior surface portion of the anterior wall. The other limb is adapted to lie adjacent, i.e. supported on an interior surface portion of the posterior vaginal wall. The base portion has an aperture which, in use, is adjacent the cervix of the uterus.

The base portion is preferably arch shaped, and is preferably comprised of a resilient material or has resilient material embedded within the arch.

Preferably, the cradle-like structure, which lifts the bladder base and bladder neck, is formed by two protrusions extending from the free end of the limb which lies adjacent the anterior vaginal wall. These protrusions have a depression therebetween. This depression accommodates the anterior vaginal wall and the neck and base of the bladder.

In use, the base portion biases the limbs outwardly to aid in retention of the device in the vagina.

The limb adjacent the posterior vaginal wall preferably has two legs at its free end. These legs are preferably curved and splayed in order to fit over the perineal body for supporting the device in the vagina.

Preferably, the opposing inner surfaces of the two limbs, are covered by a spongy deformable material bearing complementary grooves and ridges. This material imitates vaginal mucosa. Sexual intercourse is therefore not effected by the device as the spongy material cannot readily be distinguished by the male partner. Additionally, the grooves and ridges aid in channelling menstrual blood and vaginal secretions through the vagina.

A further aspect of the present invention has the object of providing an intra-vaginal device to aid in controlling urinary incontinence.

There is further disclosed herein an intra-vaginal device to aid in controlling urinary incontinence, said device comprising, a body having a forward portion to engage an anterior portion of the vaginal wall, and a rear portion to engage a posterior portion of the vaginal wall, and wherein said anterior portion is expandable to apply pressure to the bladder neck to at least partly close the neck.

Preferably the body of the above described intra-vaginal device to aid in controlling urinary incontinence, would consist of a flexible ring defining a central portion substantially closed by means of a diaphragm.

Still further, it is preferred that the above described ring would be adjustable in diameter.

The present invention will now be described by way of example only with reference to the following drawings, in which.

Figure 1:
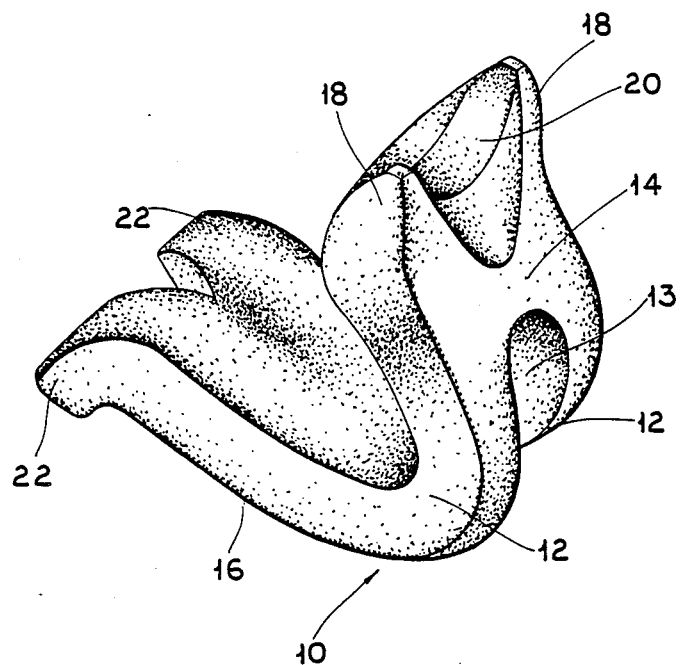
FIG. 1 is a perspective view of the intra-vaginal device.
Figure 2:
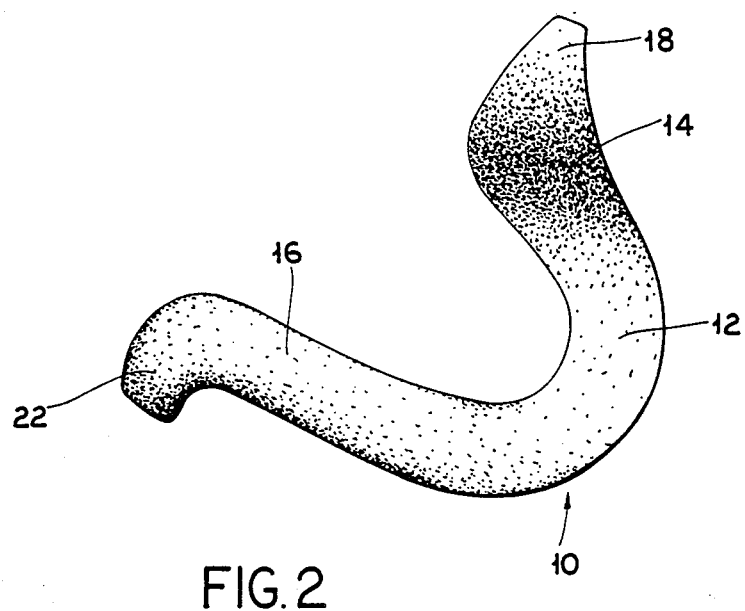
FIG. 2 is a side view of the intra-vaginal device.
Figure 3:
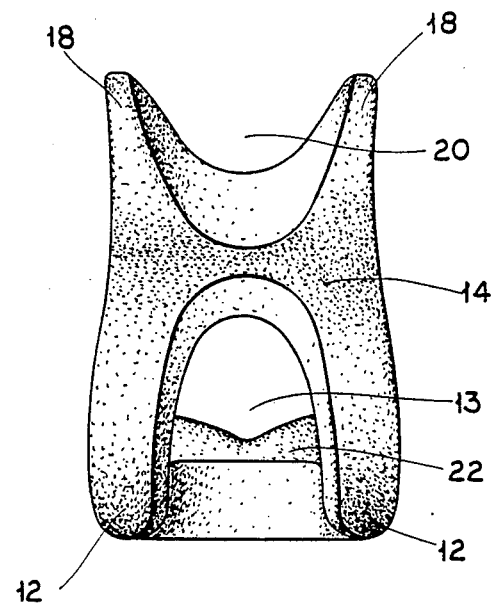
FIG. 3 is an end view of the intra-vaginal device.

The intra-vaginal device shown in FIG. 1 is constructed of a flexible material, for example a plastic/silicone compound.

The device comprises a base portion 10 which forms an arch 12 of generally "U-shaped" configuration. The base portion 10 may be inherently resilient or may contain a resilient insert. The arch 12 contains an aperture 13 which in use is adjacent the cervix of the uterus. The arch 12 interconnects two opposing limbs 14 and 16. The limb 14 lies adjacent the anterior vaginal wall in use and has at its end two opposed rounded projections 18 having a depression 20 therebetween to form a cradle-like structure.

The limb 16 extending from the arch 12 is of substantially planar construction and has at its forward end a pair of splayed legs 22.

The flexible and resilient nature of the arch 12 enables the device to be readily inserted into the vagina and aids in its retention therein. Particularly, the arch 12 biases the limbs 14 and 16 outwardly, causing them to press against the anterior and posterior walls of the vagina respectively, this holding the device in place.

Figure 4:
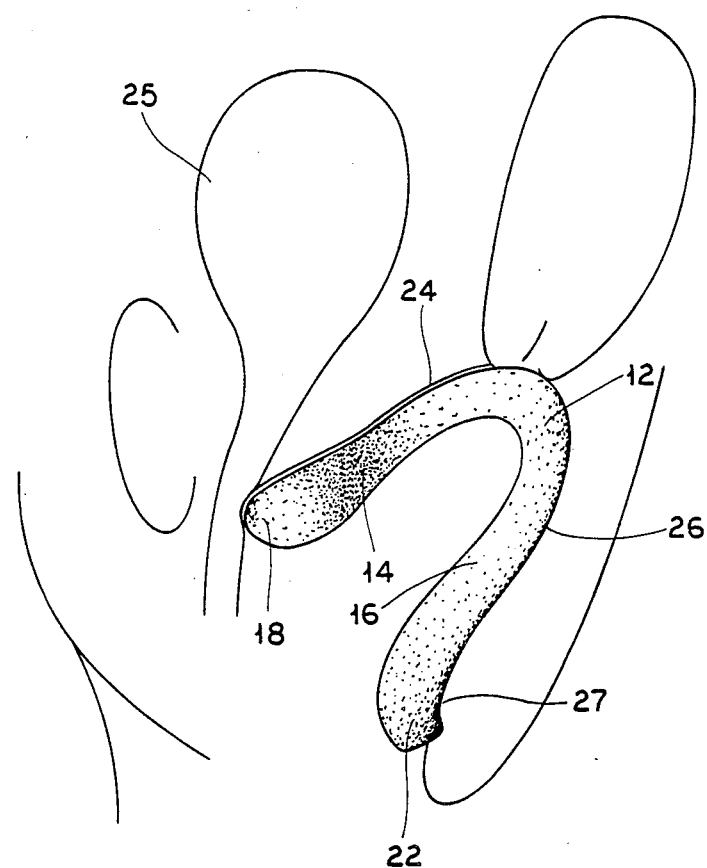
FIG. 4 is a schematic view of a saggital section of the female pelvic organs showing the intra-vaginal device in place.

As shown in FIG. 4, when the device is inserted into the vagina, the limb 14 lies adjacent to and supports the anterior vaginal wall 24 preventing prolapse of the anterior vaginal wall (cystocele) and prolapse caused by the bladder 25 pressing against the anterior vaginal wall 24 (cysto-urethrocele). The outward bias of the limb 14 causes the projections 18 to cradle the anterior vaginal wall 24 and lift the neck and base of the bladder above the pelvic floor muscle thereby causing continence. Additionally, a significant closure of the bladder neck is achieved as is a reduction of the included angle between the urethra and the bladder. These features again increase continence.

The arch 12 supports the cardinal and uterosacaral ligaments (not shown) and helps to lift the uterus in the pelvic cavity thereby preventing uterine prolapse. The aperture 13 in the arch 12 lies adjacent the cervix of the uterus.

The limb 16 lies adjacent to and supports the posterior vaginal wall 26, thereby preventing prolapse of the posterior vaginal wall 26 (enterocele) and rectal prolapse (retocele). The legs 22 of the limb 14 rest on the posterior vaginal wall 26 in the region of the para-rectal fossa 27. The splayed nature of the legs enables them to fit over the perineal body, this aiding in retention of the device in the vagina.

The device may be of different sizes to accommodate different vaginal size. Preferably, those portions of the device contacting the vaginal wall are smeared with Disaestrol and Sultril cream in order to minimize vaginal irritation.

Figure 5:
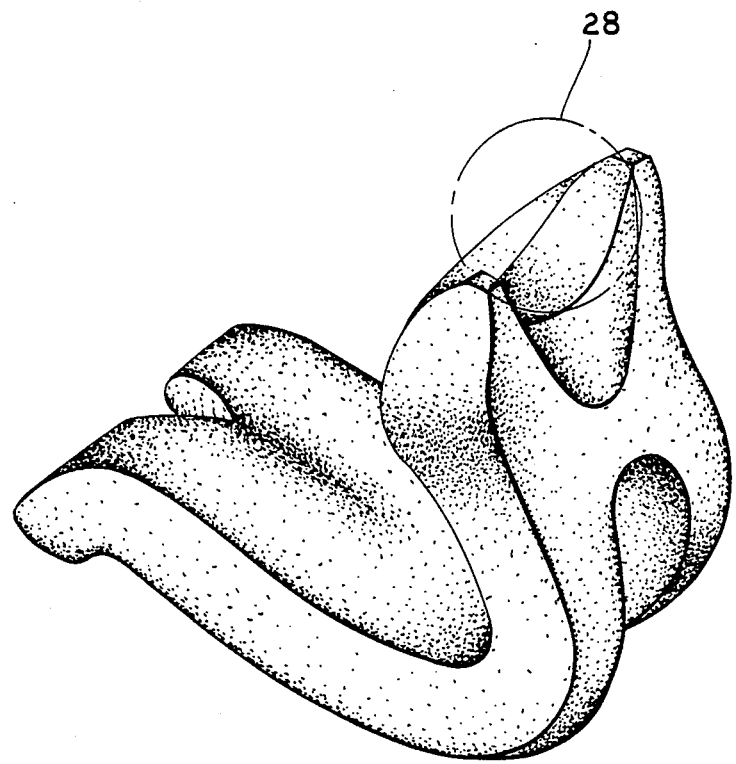
FIG. 5 is a schematic perspective view of an intra-vaginal device to aid in controlling urinary incontinence.
Figure 6:
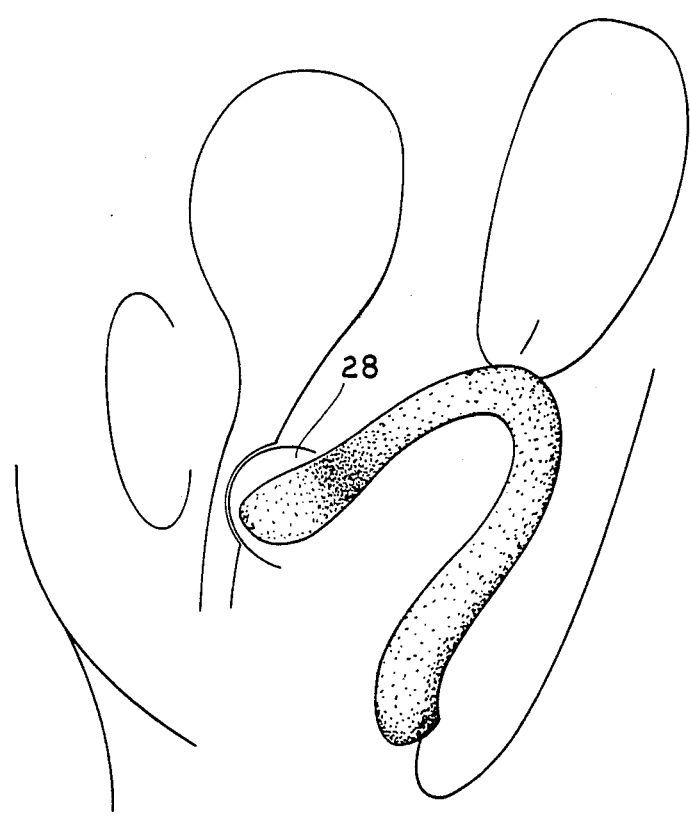
FIG. 6 is a schematic view of a saggital section of the female pelvic organs showing the device of FIG. 5 in place.

In a further embodiment of the present invention as shown in FIGS. 5 and 6, a small inflatable balloon 28 may be provided between the projections 18. The balloon may be inflated to compress the bladder neck against the public symphasis thus closing off the urethra resulting in continence. The balloon 18 may be inflated/deflated by virtue of a small lead connected to the balloon which passes out of the vagina where it can be manipulated by the patient.

Figure 7:
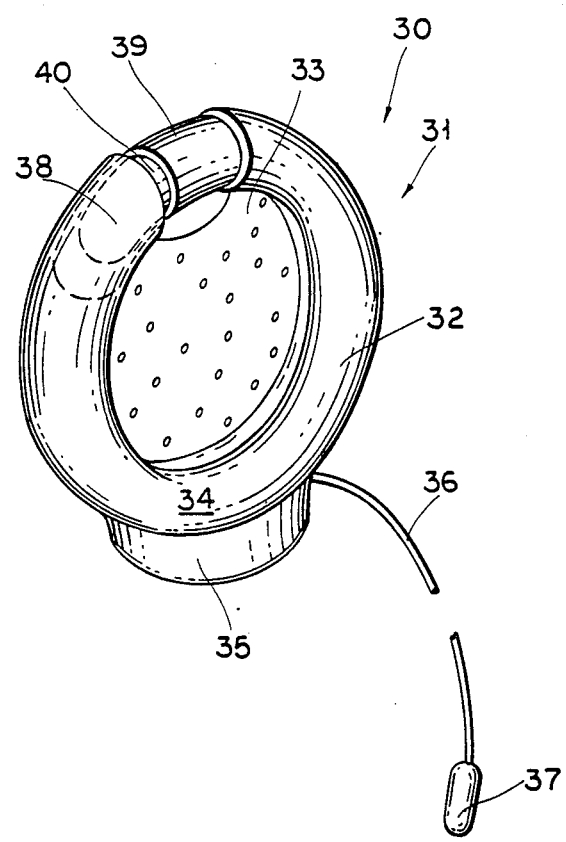
FIG. 7 is a schematic perspective view of an intra-vaginal device to aid in controlling urinary incontinence.

In FIG. 7 there is schematically depicted an intra-vaginal device to aid in controlling urinary incontinence. The device 30 includes a body 31 which is formed of a ring member 32 of generally resilient material. The ring member 32 defines a central cavity closed by means of a flexible diaphragm 33.

The forward portion 34 of the ring member 32 is provided with an expandable portion 35 which in this particular embodiment is inflated by means of inserting air under pressure within a cavity defined by the expandable member 35. Air under pressure is delivered to the cavity by means of a flexible line 36 extending to a one way valve 37. The one way valve 37 would be actuable to allow deflation of the expandable member 35. In FIG. 7, the expandable member 35 is shown as inflated.

The rear portion 38 of the ring member 32 is provided with a rotatable threaded sleeve 39 which engages a threaded shaft 40 so that upon rotation of the sleeve 39, the ring member 32 may be increased or decreased in effective diameter.

In operation of the above described device 30, the device 30 is positioned within the vagina so that the forward portion 34 is located adjacent the bladder neck. The rear portion 38 is located on the posterior portion of the vaginal wall. When the expandable member 35 is inflated, the expandable member lifts the bladder neck as well as applies a compression force to the bladder neck to close the bladder neck. To enable the user to urinate, the one way valve 37 is operated to allow deflation of the expandable member 35 to again allow the bladder neck to open.

The diaphragm 33 is relatively thin and pliable and is perforated to allow for the discharge of menstrual blood and vaginal secretions.

The above discussed preferred embodiments of the present invention have the advantage that they may be placed in position by a medical practitioner without anaesthetic, with immediate results achievable.

What I claim is:

1. An entirely intra-vaginal device, comprising two opposed limbs interconnected by a flexible base portion so as to be of an upwardly convex generally "U-shaped" configuration, one of the limbs being adapted to lie adjacent the anterior vaginal wall and including a cradle-like structure to lift the bladder base and bladder neck, lying behind the vaginal wall, without closing the urethra, the other limb being adapted to lie adjacent the posterior vaginal wall, and the base portion having an aperture which, in use, is adjacent the cervix of the uterus.

2. The device of claim 1 wherein the device is formed of a resilient material.

3. The device of claim 1 wherein said cradle-like structure is formed by two protrusions extending from the free end of the limb which lies adjacent the anterior vaginal wall.

4. The device of claim 3 wherein the protrusions have a depression therebetween.

5. The device of claim 4 wherein the base portion biases the limbs outwardly to aid in retaining the device within the vagina.

6. The device of claim 1 wherein the limb to lie adjacent the posterior vaginal wall has two legs at its free end, with the legs being curved and splayed so that in use the legs fit over the perineal body for supporting the device in the vagina.

7. The device of claim 1 wherein the limb which engages the anterior vaginal wall is provided with an expandable member to at least partly close the bladder neck.

8. An entirely intra-vaginal device, comprising:
 a first limb for being supported only on an interior surface portion of a posterior vaginal wall;
 a second limb;
 a flexible base portion connecting the first and second limbs to form the limbs and base portion into a generally U-shaped configuration, the base portion having an aperture positioned for being adjacent a cervix of a uterus when the first limb is supported on the interior surface portion of the posterior vaginal wall; and
 a cradle-like structure on the second limb for engaging an interior surface portion of an anterior vaginal wall when the first limb is supported on the interior surface portion of the posterior vaginal wall and supporting a base and neck of a bladder located at an exterior surface portion of the anterior vaginal wall opposite the interior surface portion of the anterior vaginal wall without closing a urethra connected to the bladder.

9. An entirely intra-vaginal device having an anterior portion to engage the anterior vaginal wall and a posterior portion to engage the posterior vaginal wall, said device being of a generally arcuate configuration so as to be upwardly convex and being formed of a resilient material so that in use it may be resiliently deformed and therefore bias the anterior and posterior portions into contact with the vaginal wall to retain the device in position within the vagina, and wherein said anterior portion has a cradle which in use lifts the bladder and bladder neck, without closing the urethra, lying behind the anterior vaginal wall.

10. The device of claim 9 having a central body portion extending between the anterior and posterior portions, which central body portion has an aperture to be positioned adjacent the cervix.

11. The device of claim 9 wherein said cradle is provided by a pair of transversely spaced projections between which there is defined a depression through which, in use, the bladder neck passes to the cradle by the projections.

12. The device of claim 11 wherein said posterior portion has a pair of rearwardly projecting legs which in use fit over the perineal body for supporting the device in the vagina.

* * * * *